(12) United States Patent
Rezvani et al.

(10) Patent No.: US 9,488,611 B2
(45) Date of Patent: Nov. 8, 2016

(54) LOW-CONDUCTIVITY CONTACTING-TYPE CONDUCTIVITY MEASUREMENT

(71) Applicant: Rosemount Analytical Inc., Irvine, CA (US)

(72) Inventors: Behzad Rezvani, Anaheim, CA (US); Jeffrey Lomibao, Corona, CA (US)

(73) Assignee: Rosemount Analytical Inc., Irvine, CA (US)

( * ) Notice: Subject to any disclaimer, the term of this patent is extended or adjusted under 35 U.S.C. 154(b) by 251 days.

(21) Appl. No.: 13/743,811

(22) Filed: Jan. 17, 2013

(65) Prior Publication Data

US 2013/0187673 A1   Jul. 25, 2013

Related U.S. Application Data

(60) Provisional application No. 61/588,934, filed on Jan. 20, 2012.

(51) Int. Cl.
*G01N 27/06* (2006.01)

(52) U.S. Cl.
CPC .................. *G01N 27/06* (2013.01)

(58) Field of Classification Search
CPC .................................................. G01N 27/06
USPC ........................................................ 324/713
See application file for complete search history.

(56) References Cited

U.S. PATENT DOCUMENTS

| | | | |
|---|---|---|---|
| 4,808,930 A * | 2/1989 | Kaiser | G01N 33/18 204/406 |
| 5,504,430 A | 4/1996 | Andersson | |
| 5,708,363 A | 1/1998 | Yates et al. | |
| 6,278,281 B1 | 8/2001 | Bauer et al. | |
| 6,369,579 B1 | 4/2002 | Riegel | |
| 6,377,052 B1 | 4/2002 | McGinnis et al. | |
| 6,782,736 B1 | 8/2004 | Hammer | |

(Continued)

FOREIGN PATENT DOCUMENTS

| | | |
|---|---|---|
| DE | 4233110 A1 | 4/1994 |
| DE | 19815922 A1 | 10/1999 |

(Continued)

OTHER PUBLICATIONS

"Using the DMM Series to make simple and accurate resistance measurements", Tektronix Application Note, copyright (c) 2009, Tektronix.*

(Continued)

*Primary Examiner* — Vincent Q Nguyen
(74) *Attorney, Agent, or Firm* — Christopher R. Christenson; Kelly, Holt & Christenson, PLLC

(57) ABSTRACT

A method of measuring low conductivity of a liquid sample using a contacting-type conductivity sensor is provided. The method includes applying a first excitation current to a contacting-type conductivity sensor at a first drive frequency. A first voltage response to the first excitation current is determined. A second excitation current is applied to the contacting-type conductivity sensor at a second drive frequency higher than the first drive frequency. A second voltage response to the second excitation current is determined. A conductivity output is provided based, at least in part, on the first and second voltage responses. A system for measuring conductivity of a liquid at or below 100 μS/cm is also provided.

11 Claims, 4 Drawing Sheets

(56) References Cited

U.S. PATENT DOCUMENTS

| | | | |
|---|---|---|---|
| 7,772,854 B2 | 8/2010 | Rezvani | 324/691 |
| 8,063,644 B2 | 11/2011 | Rezvani | 324/438 |
| 2004/0251919 A1 | 12/2004 | Stahlmann et al. | |
| 2007/0024287 A1* | 2/2007 | Graves et al. | 324/453 |
| 2008/0061804 A1* | 3/2008 | Rezvani | 324/722 |
| 2008/0252296 A1* | 10/2008 | Hu et al. | 324/366 |

FOREIGN PATENT DOCUMENTS

| | | |
|---|---|---|
| EP | 0911639 | 4/1999 |
| WO | WO 2008/021546 | 2/2008 |
| WO | WO 2008/030585 | 3/2008 |

OTHER PUBLICATIONS

Search Report and Written Opinion from corresponding International patent application No. PCT/US13/022042 dated Apr. 19, 2013.

"Dual-Input Intelligent Analyzer, Model 1056," Product Data Sheet PDS 71/1056/rev.B, Emerson Process Management, Feb. 2007, 12 pages.

Theory are Application of Conductivity, Application Data Sheet ADS 43-018/rev.B, Emerson Process Management, Aug. 2004, 5 pages.

First Examiner Report for counterpart Australian Patent Application No. 2013209704 dated Aug. 5, 2014, 3 pages.

First Office Action ffrom Chinese Patent Application No. 201380005980.8, dated May 25, 2015, 18 pages.

Patent Examination Report No. 2 from Australian Patent Application No. 2013209704, dated Jun. 19, 2015, 3 pages.

Office Action for Canadian Patent Application No, 2,862,183 dated Dec. 15, 2015, 4 pages.

Second Office Action for Chinese Patent Application No. 201380005980.8 dated Dec. 28, 2015, 20 pages.

Third Office Action for Chinese Patent Application No. 201380005980.8 dated Jun. 22, 2016, 24 pages.

* cited by examiner

LOW-CONDUCTIVITY CONTACTING-TYPE CONDUCTIVITY MEASUREMENT

CROSS-REFERENCE TO RELATED APPLICATION

The present application is based on and claims the benefit of U.S. provisional patent application Ser. No. 61/588,934, filed Jan. 20, 2012, the content of which is hereby incorporated by reference in its entirety.

BACKGROUND

Liquid conductivity measurement systems are used for the measurement of conductivity of water and aqueous or non-aqueous solutions in environmental, medical, industrial, and other applications where an indication of the ionic content of the liquid is required.

Liquid conductivity is measured in a variety of contexts to provide a relatively inexpensive parameter that can be sometimes related to bulk ionic concentration. In situations where a single type of ion is present, the conductivity can actually be related to specific ionic concentration. Even in situations where a number of different ionic compounds are present, the measurement of bulk liquid conductivity can still provide very useful information. Accordingly, there has been widespread adoption and utilization of conductivity measurement by the industry for a variety of different purposes. Given the variety of different applications for such systems, it is expected that some will be employed to provide conductivity measurements for low-conductivity liquids, while others will be employed to provide conductivity measurements for high-conductivity liquids.

Typically, contact-based conductivity measurement systems include a conductivity sensor or cell and an associated conductivity analyzer or meter. FIG. 1 illustrates such a system. A conductivity meter generates an AC current through electrodes of the conductivity cell. The meter then senses the resultant voltage between the electrodes of the cell. This voltage is generally a function of the conductivity of the liquid to which the cell is exposed.

The voltage between the electrodes depends not only on the solution conductivity, but also on the length, surface area, and geometry of the sensor electrodes. The probe constant (also called sensor constant or cell constant) is a measure of the response of a sensor to a conductive solution, due to the sensor's dimensions and geometry. Its units are $cm^{-1}$ (length divided by area), and the probe constant necessary for a given conductivity range is based on the particular conductivity analyzer's measuring circuitry. Probe constants can vary from 0.01 $cm^{-1}$ to 50 $cm^{-1}$ and, in general, the higher the conductivity, the larger the probe constant necessary.

SUMMARY

A method of measuring low conductivity of a liquid sample using a contacting-type conductivity sensor is provided. The method includes applying a first excitation current to a contacting-type conductivity sensor at a first drive frequency. A first voltage response to the first excitation current is determined. A second excitation current is applied to the contacting-type conductivity sensor at a second drive frequency higher than the first drive frequency. A second voltage response to the second excitation current is determined. A conductivity output is provided based, at least in part, on the first and second voltage responses. A system for measuring conductivity of a liquid at or below 100 µS/cm is also provided.

DETAILED DESCRIPTION OF ILLUSTRATIVE EMBODIMENTS

Four electrode conductivity sensors are typically used for high conductivity measurements, but they become excessively nonlinear at low conductivities. Two of the electrodes are used to drive a current through the liquid. The other two electrodes are used to sense the voltage developed across the liquid. Generally a four-electrode conductivity sensor connects to a conductivity analyzer or other suitable instrument via a multi-conductor cable. When measuring low conductivities (100 µS/cm or lower), the source impedance of the solution and the capacitance of the cable distort the voltage waveform and cause significant error in the measurement. The voltage waveform distortion is related to the time constant formed by the source impedance R and the cable capacitance C. In some cases, a reduction in the measurement frequency is used such that the time constant formed by RC is much smaller than the signal period (T). While reducing the drive frequency can reduce such errors, such an approach may not be suitable for all applications. For example, reducing the drive frequency may introduce additional sources of noise in environments with significant 50/60 Hz AC devices or other sources of low-frequency interference.

Embodiments of the present invention generally provide a method of providing a more accurate low-conductivity sensor measurement without the necessity of using a lower drive frequency. As used herein, a "low-conductivity" value is any value that is equal to or less than 100 µS/cm. As set forth above, for such low measurements, the source impedance and the cable capacitance are significant sources of error. In such instances, embodiments of the present invention can be employed to provide a more accurate conductivity measurement without employing a lower frequency drive current.

Figure 1:
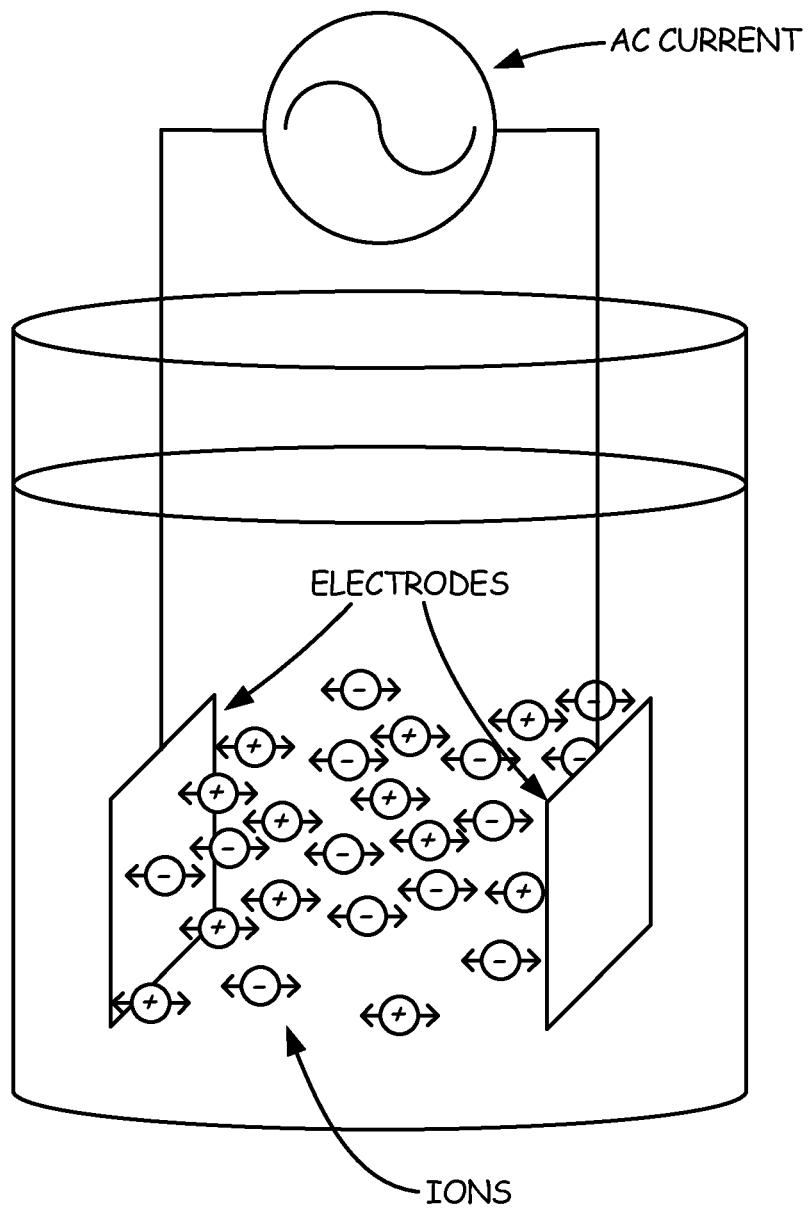
FIG. 1 is a diagrammatic view of a contacting-type conductivity measurement system.
Figure 2:
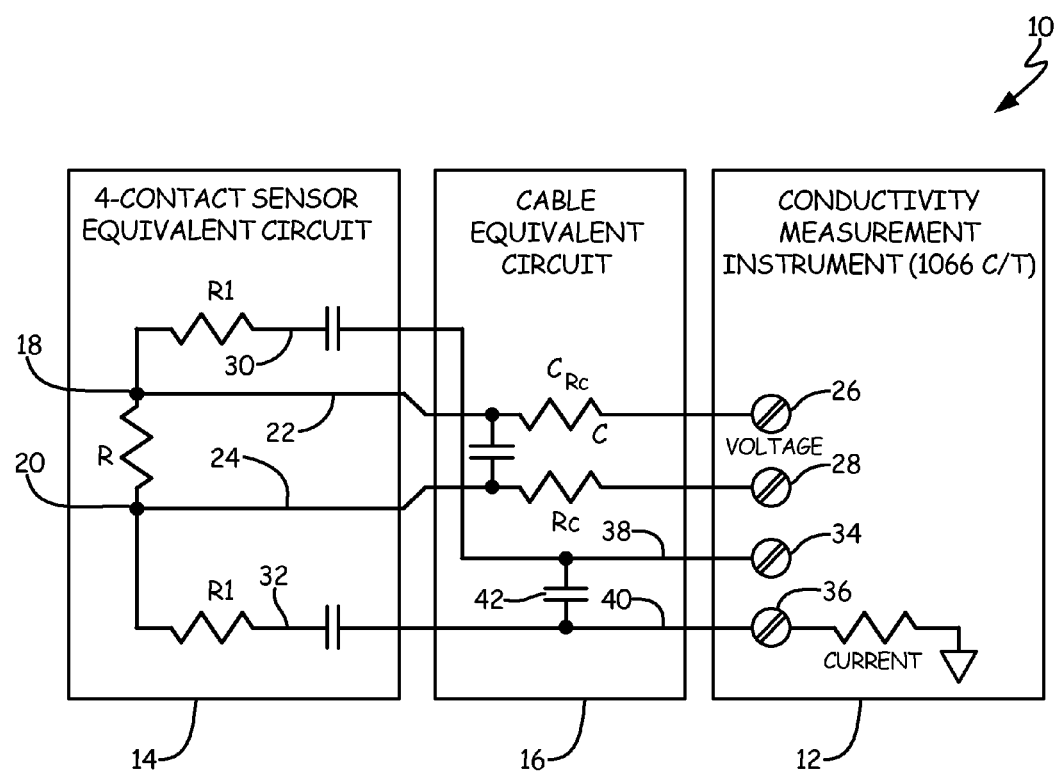
FIG. 2 is a diagrammatic view of a four-electrode contacting-type conductivity measurement system with which embodiments of the present invention are particularly useful.

FIG. 2 is a diagrammatic view of a four-electrode contacting-type conductivity measurement system 10 with which embodiments of the present invention are particularly useful. System 10 includes conductivity analyzer 12 coupled to contacting-type four electrode conductivity sensor 14 through cable 16. Sensor 14 includes a pair of electrodes 18, 20 that contact a liquid. Electrodes 18, 20 are coupled to leads 22, 24 that are connected to voltage measurement terminals 26, 28 of analyzer 12, respectively. Electrodes 18, 20 are also coupled to leads 30, 32 which are coupled to current drive terminals 34, 36 of analyzer 12 through cable 16. The various leads and cable 16 are modeled electrically in FIG. 2 as resistances and capacitances. For example, as the insulation between conductors 38 and 40 changes in cable 16, the capacitance of equivalent capacitor 42 will change.

In operation, analyzer 12 will drive a current through conductors 38, 40 and thus through electrodes 18, 20. The current flow through the liquid sample will generate a voltage across electrodes 18, 20 which is measured by analyzer 12 at terminals 26, 28. The measured voltage is related, by analyzer 12, to conductivity of the liquid sample, and is communicated to a user or control system. Such communication can be via local display and/or over a process communication loop or segment. Additionally, such communication may occur wirelessly, such as by using wireless process communication in accordance with a wireless process communication protocol such as the WirelessHART® standard as set forth at IEC 62591. Suitable examples of analyzer 12 include that sold under the trade designation Model 1066 Two-Wire Analytical Liquid Analyzer available from Rosemount Analytical Inc, an Emerson Process Management Company, of Irvine Calif. However, other suitable analyzers can be used in accordance with embodiments of the present invention.

Figure 3A:
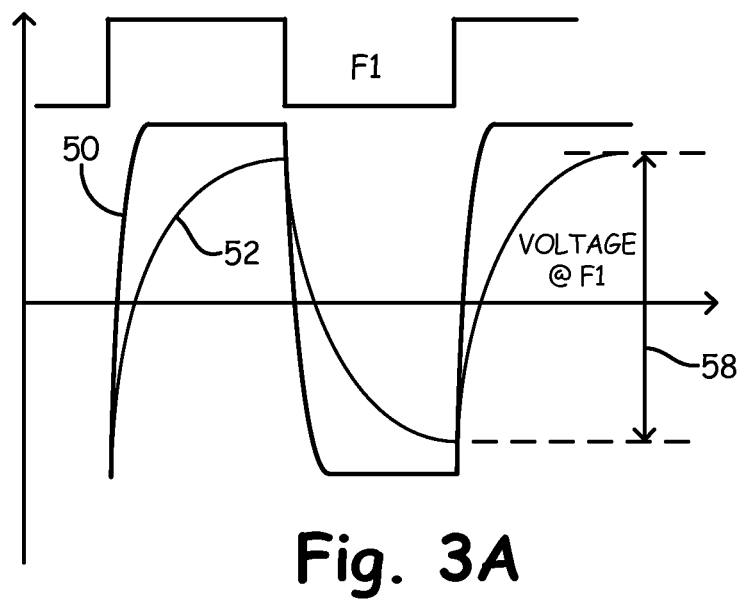
FIG. 3A is a signal chart illustrating voltage response of a contacting-type conductivity sensor when driven at frequency F1.

FIG. 3A is a signal chart illustrating voltage response of a contacting-type conductivity sensor when driven at frequency F1. When driven at frequency F1, drive current is shown at trace 50 and the voltage response trace is shown at reference numeral 52. As indicated, trace 52 has not yet reached its final value before drive polarity switches due to the time constant created by the source impedance R and the cable capacitance C. The excitation currents illustrated in FIGS. 3A and 3B are preferably square waves and also preferably pass the current in opposite directions through the liquid sample via the electrodes of the contacting-type conductivity sensor.

Figure 3B:
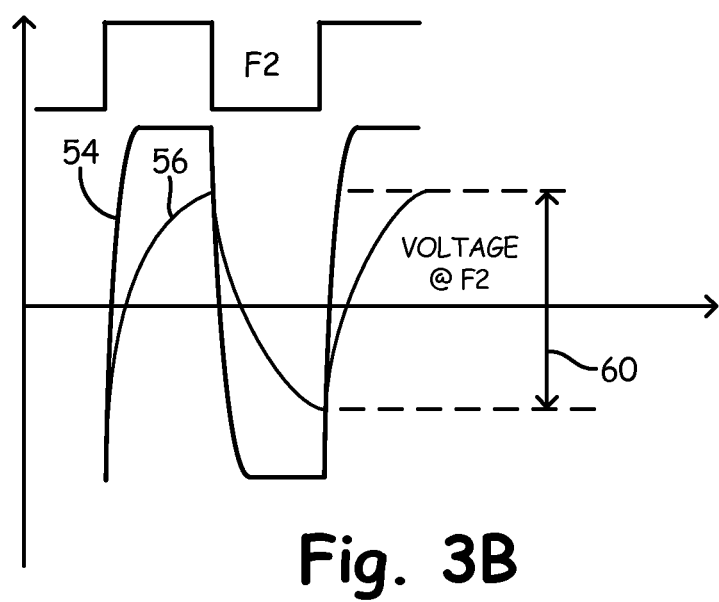
FIG. 3B is a signal chart illustrating voltage response of a contacting-type conductivity sensor when driven at frequency F2.

FIG. 3B is a signal chart illustrating voltage response of a contacting-type conductivity sensor when driven at frequency F2, which is higher than F1. When driven at frequency F2, drive current is shown at trace 54 and the voltage response trace is shown at reference numeral 56. As indicated, trace 56 has reached even less of its final value, in comparison to trace 52, before drive polarity switches. However, leveraging the two voltage responses allows an accurate calculation of conductivity. In one embodiment, the corrected voltage (i.e. the voltage that the trace would arrive at if given enough time) is calculated as the maximum peak-to-peak voltage measured or otherwise obtained on trace 52, indicated at reference numeral 58 added to a correction value. The correction value is equal to a constant (K) multiplied by the difference between peak-to-peak voltage 58 and peak-to-peak voltage 60. This is simply one function that may be used to provide the corrected voltage. Other functions can also be used in accordance with embodiments of the present invention. For example, three voltage measurements could be obtained at three distinct drive frequencies and the corrected voltage could be determined from an exponential curve fit to calculate the final corrected voltage value.

Figure 4:
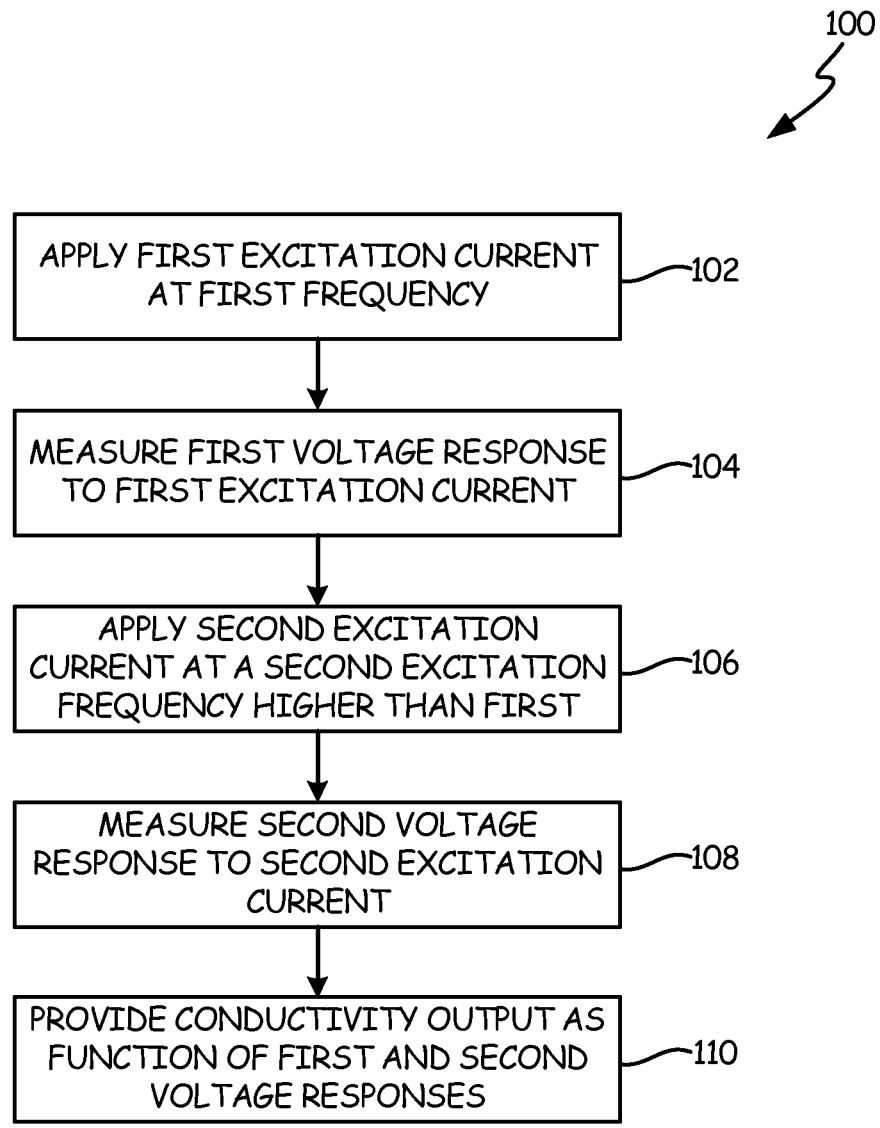
FIG. 4 is a flow diagram of a method of determining a low-conductivity value in accordance with an embodiment of the present invention.

FIG. 4 is a flow diagram of a method of determining a low-conductivity value (at or below 100 µS/cm) in accordance with an embodiment of the present invention. Method 100 begins at block 102 where a first excitation current is applied to the contacting conductivity sensor. The first current induces a voltage within the liquid sample related to the conductivity of the liquid sample. At block 104, the voltage response across a pair of measuring electrodes of the sensor is determined. This determination may simply be a measurement of the maximum peak-to-peak voltage observed during application of the first excitation current. Next, at block 106, a second excitation current is applied to the liquid sample. The second excitation current is applied at a frequency that is higher than the first excitation current. At block 108, the voltage response of the conductivity sensor to the second excitation current is determined. Next, at block 110, a conductivity output is provided as a function of the first and second voltage responses. For example, the conductivity output can be based on a corrected voltage ($V_{CORRECTED}$) that is equal to the voltage response determined during the application of the first excitation current ($V_{F1}$) plus a constant (K) multiplied by the difference in the first voltage response ($V_{F1}$) from the second voltage response ($V_{F2}$). Thus, ($V_{CORRECTED}$)=($V_{F1}$)*K(($V_{F1}$)−($V_{F2}$)). For better accuracy yet, an additional third excitation current could be used at yet a higher frequency to determine a third voltage response. The three voltage responses could then be fit to an exponential curve to calculate the final conductivity value.

Although the present invention has been described with reference to preferred embodiments, workers skilled in the art will recognize that changes may be made in form and detail without departing from the spirit and scope of the invention.

What is claimed is:

1. A method of measuring conductivity at or below 100 µS/cm of a liquid sample using a contacting-type conductivity sensor, the method comprising:
    applying a first excitation current using an analyzer, through a first pair of leads, to the contacting-type conductivity sensor at a first drive frequency, wherein the first pair of leads are placed in contact with the liquid sample having a source impedance that generates an error in conductivity measurement and wherein the excitation current at least partially extends through the liquid sample;
    determining a first voltage response through a second pair of leads of the contacting-type conductivity sensor to the first excitation current using the analyzer;
    applying a second excitation current using the analyzer, through the first pair of leads, to the contacting-type conductivity sensor at a second drive frequency different than the first drive frequency;
    determining a second voltage response through the second pair of leads of the contacting-type conductivity sensor to the second excitation current using the analyzer;
    providing a corrected conductivity output based, at least in part, on the first and second voltage responses wherein the corrected conductivity output is a function of the first and second voltage responses, and comprises a reduced error with respect to the source impedance; and
    wherein the second drive frequency is higher than the first drive frequency.

2. The method of claim 1, wherein providing a conductivity output includes calculating a correction value equal to a difference between the first and second voltage responses multiplied by a constant.

3. The method of claim 2, wherein the conductivity output is calculated by adding the first voltage response to the correction value.

4. The method of claim 1, wherein the first voltage response is a maximum peak-to-peak voltage measured across the conductivity sensor during application of the first excitation current.

5. The method of claim 4, wherein the second voltage response is a maximum peak-to-peak voltage measured across the conductivity sensor during application of the second excitation current.

6. The method of claim 1, wherein at least one of the first and second excitation currents is a square wave.

7. The method of claim 1, and further comprising:
applying a third excitation current to the contacting-type conductivity sensor at a third drive frequency higher than the second drive frequency;
determining a third voltage response to the third excitation current; and
providing a conductivity output based, at least in part, on the first, second and third voltage responses.

8. The method of claim 7, wherein providing the conductivity output includes fitting the first, second and third voltage responses to an exponential curve.

9. A system for measuring conductivity of a liquid at or below 100 μS/cm, the system comprising:
a contacting-type conductivity sensor having a plurality of electrodes configured to contact the liquid, wherein the liquid has a source impedence;
an analyzer coupled to the contacting-type conductivity sensor via a multi-conductor cable having a capacitance that generates an error in the measurement, the analyzer being configured to:
apply a first excitation current, through a first pair of leads, to the contacting-type conductivity sensor at a first drive frequency;
determine a first voltage response through a second pair of leads of the contacting-type conductivity sensor to the first excitation current;
apply a second excitation current, through the first pair of leads, to the contacting-type conductivity sensor at a second drive frequency different than the first drive frequency;
determine a second voltage response through a second pair of leads of the contacting-type conductivity sensor to the second excitation current; and
provide a corrected conductivity output based, at least in part, on the first and second voltage responses, wherein the corrected conductivity output is a function of the first and second voltage responses and comprises a reduced error with respect to the capacitance, and wherein the second drive frequency is higher than the first drive frequency.

10. The system of claim 9, wherein the analyzer is further configured to:
apply a third excitation current to the contacting-type conductivity sensor at a third drive frequency higher than the second drive frequency;
determine a third voltage response to the third excitation current; and
provide a conductivity output based, at least in part, on the first, second and third voltage responses.

11. The method of claim 10, wherein providing the conductivity output includes fitting the first, second and third voltage responses to an exponential curve.

* * * * *